United States Patent
Malhotra et al.

(10) Patent No.: US 11,478,483 B2
(45) Date of Patent: Oct. 25, 2022

(54) METHOD OF TREATING HYPERTENSION

(71) Applicant: Cipla Limited, Mumbai (IN)

(72) Inventors: Geena Malhotra, Mumbai (IN);
Kalpana Joshi, Maharashtra (IN);
Jeevan Ghosalkar, Mahrashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 16/123,553

(22) Filed: Sep. 6, 2018

(65) Prior Publication Data
US 2019/0076441 A1 Mar. 14, 2019

(30) Foreign Application Priority Data

Sep. 8, 2017 (IN) .............. 201721031870

(51) Int. Cl.
*A61K 31/554* (2006.01)
*A61K 45/06* (2006.01)
*A61P 9/12* (2006.01)

(52) U.S. Cl.
CPC ............ *A61K 31/554* (2013.01); *A61K 45/06* (2013.01); *A61P 9/12* (2018.01)

(58) Field of Classification Search
CPC .................................................. A61K 31/554
See application file for complete search history.

(56) References Cited

U.S. PATENT DOCUMENTS

| 2006/0235005 A1* | 10/2006 | Goff | ..................... A61K 31/445 514/220 |
| 2009/0239883 A1* | 9/2009 | Butrous | ................... A61P 17/00 514/262.1 |
| 2010/0099707 A1* | 4/2010 | Amer | ..................... A61P 11/00 514/315 |

FOREIGN PATENT DOCUMENTS

EP 2438920 A1 * 4/2012 .......... A61K 9/2054

OTHER PUBLICATIONS

Suzuki et al (International Journal of Cardiology vol. 207 pp. 363-364. Published online Jan. 7, 2016) (Year: 2016).*
Jones et al., (Am. J. Psychiatry vol. 157 pp. 148-149. Published 2000). (Year: 2000).*
Miyata et al., (Lung vol. 178 pp. 63-73. Published 2000). (Year: 2000).*
Miyata et al (Lung vol. 178 pp. 63-73 pp. 2000) (Year: 2000).*
Jones (Am. J. Psychiatry vol. 157 pp. 148-149. Published 2000) (Year: 2000).*
Jensen et al (Nueropyschopharmacology vol. 33 pp. 2303-2312 published 2008) (Year: 2008).*
Dumitrascu (European Respiratory Journal vol. 37 p. 1104-1118 published 2011) (Year: 2011).*
Reagan-Shaw et al. (FASEBJ vol. 22 pp. 659-661 published 2007) (Year: 2007).*

* cited by examiner

*Primary Examiner* — Theodore R. Howell
*Assistant Examiner* — George W Kosturko
(74) *Attorney, Agent, or Firm* — Meunier Carlin & Curfman LLC

(57) ABSTRACT

Disclosed herein are compositions and methods for the treatment of pulmonary hypertension, including pulmonary arterial hypertension. The methods include administering to a patient in need thereof an effective amount of Quetiapine or derivative thereof. The compositions include an effective amount of Quetiapine or derivative thereof, in some instances combined with one or more additional agents for the treatment of pulmonary hypertension.

13 Claims, 3 Drawing Sheets

METHOD OF TREATING HYPERTENSION

CROSS-REFERENCE TO RELATED APPLICATION

This application claims the benefit of Indian Application 201721031870, filed on Sep. 8, 2017, the contents of which are hereby incorporated in its entirety.

FIELD OF THE INVENTION

The present invention relates to a method of treatment of pulmonary hypertension, including pulmonary arterial hypertension, by administering quetiapine either alone or optionally in combination with one or more other agents. The present invention also pertains to compositions and kits useful for the treatment of pulmonary arterial hypertension in humans containing quetiapine or derivative thereof, alone or in combination with one or more drugs.

BACKGROUND

Pulmonary arterial hypertension (PAH), one of the five types of pulmonary hypertension (PH), is a life-threatening disease characterized by pulmonary vascular remodeling that leads to increased pulmonary vascular resistance and pulmonary arterial pressure, most often resulting in right-side heart failure. It is a progressive condition characterized by elevated pulmonary arterial pressures leading to right ventricular (RV) failure. It is defined at cardiac catheterization as a mean pulmonary artery pressure of 25 mm Hg or more. The most common symptom associated is breathlessness, with impaired exercise capacity as a hallmark of the disease.

PAH is associated with significant morbidity and mortality. It is caused by complex pathways that culminate in structural and functional alterations of the pulmonary circulation and increases in pulmonary vascular resistance and pressure. Many mechanisms can lead to elevation of pulmonary pressures. In PAH, progressive narrowing of the pulmonary arterial bed results from an imbalance of vasoactive mediators, including prostacyclin, nitric oxide, and endothelin-1. This leads to an increased right ventricular afterload, right heart failure, and premature death. Diverse genetic, pathological, or environmental triggers stimulate PAH pathogenesis culminating in vasoconstriction, cell proliferation, vascular remodeling, and thrombosis. Current concepts suggest that PAH pathogenesis involves three primary processes: vasoconstriction, cellular proliferation/vascular remodeling, and thrombosis.

The molecular mechanism underlying PAH pathophysiology is not known yet, but it is believed that the endothelial dysfunction results in a decrease in the synthesis of endothelium-derived vasodilators such as nitric oxide and prostacyclin. Moreover, stimulation of the synthesis of vasoconstrictors such as thromboxane and vascular endothelial growth factor (VEGF) results in a severe vasoconstriction and smooth muscle and adventitial hypertrophy characteristic of patients with PAH.

Between 11% and 40% of patients with Idiopathic pulmonary arterial hypertension [IPAH] and 70% of patients with a family history of PAH carry a mutation in the gene encoding bone morphogenetic receptor-2 (BMPR2). However, penetrance is low, carriers have a 20% lifetime risk of developing pulmonary hypertension. Therefore, "multiple hits" are probably needed for the development of PAH. In pulmonary hypertension associated with left heart disease (PH-LHD), raised left atrial pressures result in secondary elevation of pulmonary pressure. In pulmonary hypertension owing to lung disease or hypoxia (PH-Lung), raised pulmonary arterial pressures result from mechanisms such as vascular destruction and hypoxic vasoconstriction. In chronic thromboembolic pulmonary hypertension [CTEPH], mechanical obstruction of the pulmonary vascular bed, is the primary process. Incidences are estimated to be 1-3.3 per million per year for IPAH and 1.75-3.7 per million per year for CTEPH; the prevalence of PAH is estimated at 15-52 per million. Pulmonary hypertension is more common in severe respiratory and cardiac disease, occurring in 18-50% of patients assessed for transplantation or lung volume reduction surgery, and in 7-83% of those with diastolic heart failure.

While there is currently no cure for PAH significant advances in the understanding of the pathophysiology of PAH have led to the development of several therapeutic targets. Besides conservative therapeutic strategies such as anticoagulation and diuretics, the current treatment paradigm for PAH targets the mediators of the three main biologic pathways that are critical for its pathogenesis and progression: (1) endothelin receptor antagonists inhibit the upregulated endothelin pathway by blocking the biologic activity of endothelin-1; (2) phosphodiesterase-5 inhibitors prevent breakdown and increase the endogenous availability of cyclic guanosine monophosphate, which signals the vasorelaxing effects of the down regulated mediator nitric oxide; and (3) prostacyclin derivatives provide an exogenous supply of the deficient mediator prostacyclin.

There are various drugs approved for the treatment of PAH: inotropic agents such as digoxin aids in the treatment by improving the heart's pumping ability. Nifedipine (Procardia) and Diltiazem (Cardizem) act as vasodilators and lowers pulmonary blood pressure and may improve the pumping ability of the right side of the heart Bosentan (Tracleer), ambrisentan (Letairis), macitentan (Opsumit), etc. are dual endothelin receptor antagonist that help to block the action of endothelin, a substance that causes narrowing of lung blood vessels. There are others which dilate the pulmonary arteries and prevent blood clot formation. Examples of such drugs are Epoprostenol (Veletri, Flolan), treprostinil sodium (Remodulin, Tyvaso), iloprost (Ventavis); PDE 5 inhibitors such as Sildenafil (Revatio), tadalafil (Adcirca), relax pulmonary smooth muscle cells, which leads to dilation of the pulmonary arteries.

Sildenafil is shown to be efficacious in therapy for humans with pulmonary arterial hypertension (Anna R Hemmes et al J. Expert Review of Cardiovascular Therapy, 4(3), 293-300, 2006)

U.S. Pat. No. 5,570,683 discloses methods for treating or preventing reversible pulmonary vasoconstriction in a mammal such as PAH using combination of inhaled nitric oxide and therapeutically-effective amount of a phosphodiesterase inhibitor; wherein said phosphodiesterase inhibitor is administered before, during, or immediately after nitric oxide administration.

U.S. Pat. No. 7,893,050 discloses therapeutic combinations, comprising an effective amount of fasudil and sildenafil, for treating pulmonary arterial hypertension.

European Patent No. EP 1097711B1 discloses the use of sildenafil in the manufacture of a medicament for treating or preventing pulmonary hypertension.

U.S. Pat. No. 8,324,247 discloses methods for treating pulmonary arterial hypertension (PAH) by blocking both 5-HT2A and 5-HT2B receptors in a pulmonary artery such as N-methyl-L-prolinol.

U.S. Pat. Nos. 9,474,752 and 8,377,933 disclose methods for treating a pulmonary hypertension condition in a human patient, using combination of ambrisentan and agent selected from the group consisting of sildenafil, tadalafil and vardenafil.

Histamine stimulates only H1- and H2-receptors, since combined H1- and H2-receptor antagonism prevented almost all of the cardiovascular actions of histamine. (Tucker A. et al American J of Physiology, 229, 1008-1013, October 1975).

In addition to these established current therapeutic options, a large number of potential therapeutic targets are being investigated. These novel therapeutic targets include soluble guanylyl cyclase, phosphodiesterases, tetrahydrobiopterin, 5-hydroxytryptamine (serotonin) receptor 2B, vasoactive intestinal peptide, receptor tyrosine kinases, adrenomedullin, rho kinase, elastases, endogenous steroids, endothelial progenitor cells, immune cells, bone morphogenetic protein and its receptors, potassium channels, metabolic pathways, and nuclear factor of activated T cells.

Despite a certain success achieved in recent years, many patients with PAH are not adequately managed with existing therapies.

It is an object of the invention to provide a novel therapeutic method for the treatment of pulmonary hypertension, including pulmonary arterial hypertension.

It is an object of the invention to provide novel compositions for the treatment of pulmonary hypertension, including pulmonary arterial hypertension.

It is an object of the invention to provide a novel therapeutic method for the treatment of pulmonary hypertension, including pulmonary arterial hypertension, using quetiapine.

It is an object of the invention to provide novel compositions for the treatment of pulmonary hypertension, including pulmonary arterial hypertension, containing quetiapine.

SUMMARY

Disclosed herein are methods for treating pulmonary hypertension, for instance, pulmonary arterial hypertension, in patients in need thereof. In some instances, the methods include at least partial reduction of the symptoms associated with pulmonary hypertension, and in some instances include completed elimination of the symptoms associated with pulmonary hypertension. The methods include the use of quetiapine or a derivative thereof for the treatment of pulmonary hypertension. Also disclosed herein are compositions for the treatment of hypertension, wherein the compositions include quetiapine or a derivative thereof.

The details of one or more embodiments are set forth in the descriptions below. Other features, objects, and advantages will be apparent from the description and from the claims.

DETAILED DESCRIPTION

Figure 1:
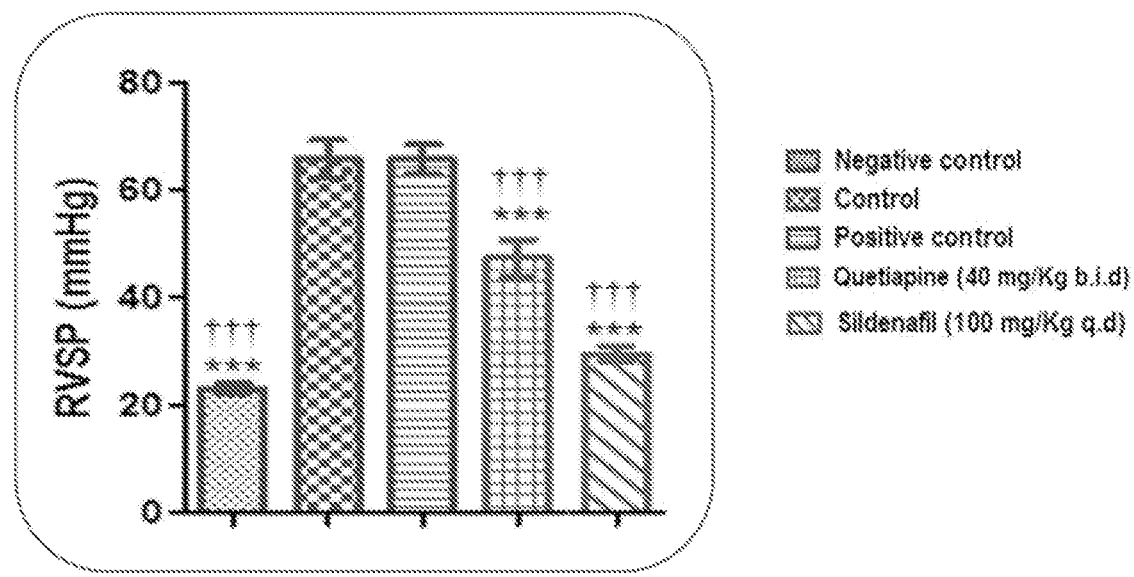
FIG. 1 depicts Right Ventricular Systolic Pressure (RVSP) mmHg for Groups I, II, III, IV, V.
Figure 2:
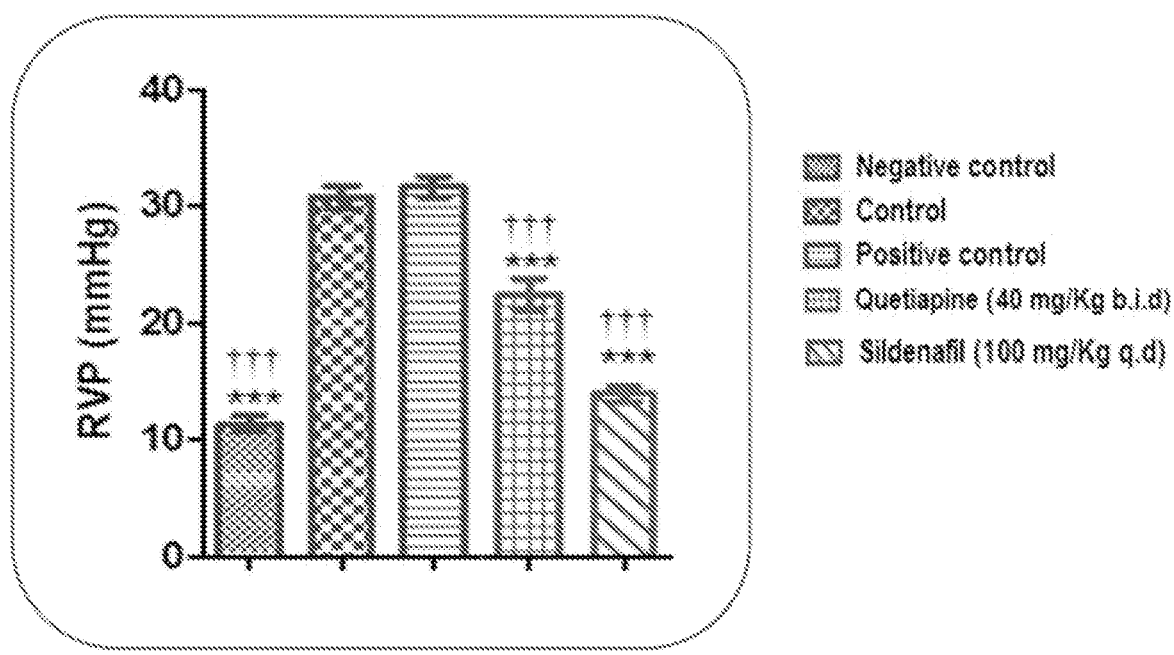
FIG. 2 depicts Right Ventricular Pressure (RVP) mmHg for Groups I, II, III, IV, V.
Figure 3:
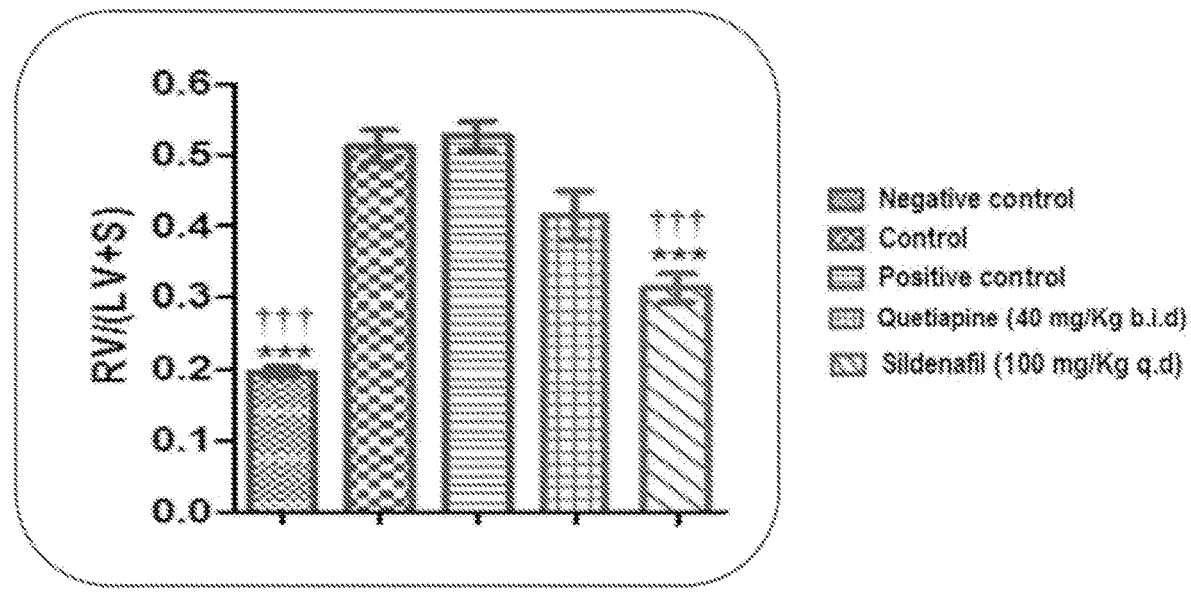
FIG. 3 depicts Fulton index: Hypertrophy (RV/LV+S) for Groups I, II, III, IV, V.
Figure 4:
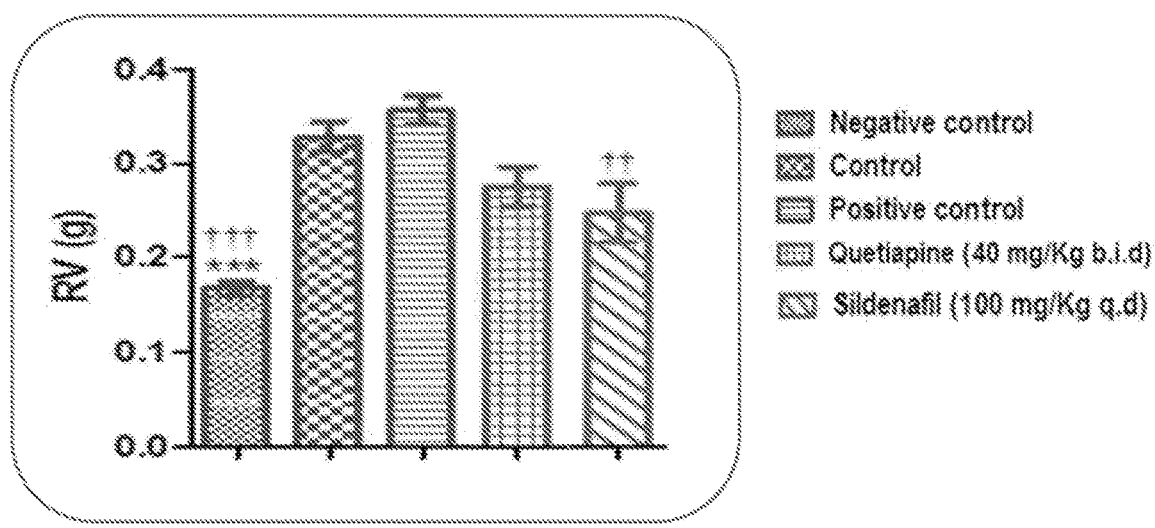
FIG. 4 depicts Right Ventricle (RV) (g) for Groups I, II, III, IV, V.
Figure 5:
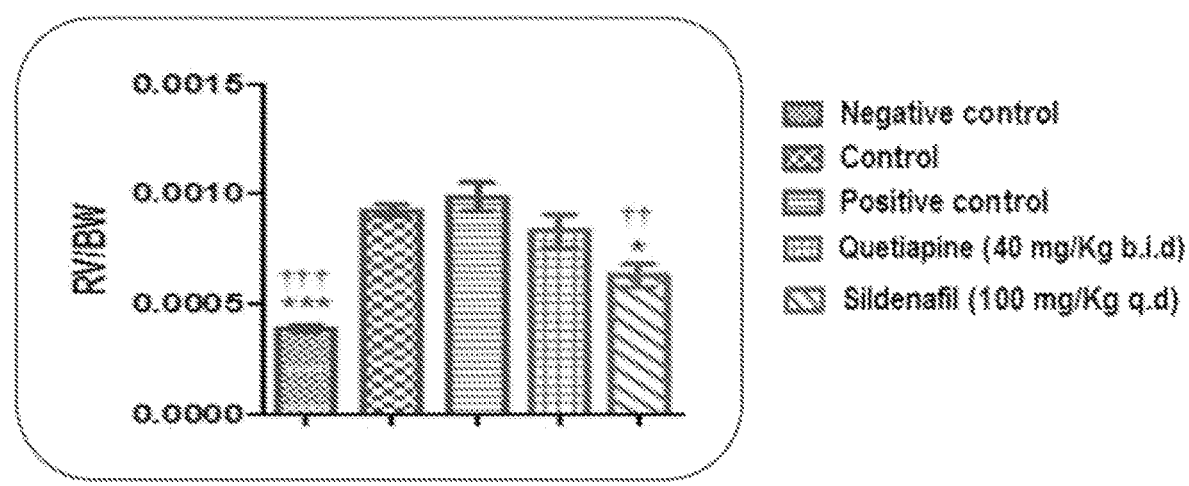
FIG. 5 depicts Right Ventricle/body Weight (RV/BW) for Groups I, II, III, IV, V.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Quetiapine is a psychotropic agent belonging to the chemical class of dibenzothiazepine derivatives, and it is used in the treatment of schizophrenia. Quetiapine fumarate is rapidly absorbed after oral administration, reaching peak plasma concentrations in 1.5 hours. Quetiapine is chemically represented as—

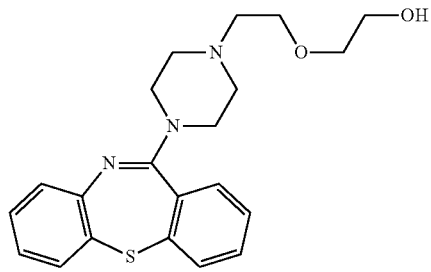 [SMILES: OCCOCCN1CCN(C2=Nc3ccccc3Sc3ccccc32)CC1]

5-HT$_{2A}$ is expressed widely throughout the central nervous system (CNS). It is expressed near most of the serotoninergic terminal rich areas, including neocortex (mainly prefrontal, parietal, and somatosensory cortex) and the olfactory tubercle. Especially, high concentrations of this receptor on the apical dendrites of pyramidal cells in layer V of the cortex may modulate cognitive processes, working memory and attention. In the periphery, it is highly expressed in platelets and many cell types of the cardiovascular system, in fibroblasts, and in neurons of the peripheral nervous system. The efficacy of Quetiapine in schizophrenia and its mood stabilizing properties in bipolar depression and mania are mediated through combination of dopamine type 2 (D2) and serotonin type 2 (5HT2) antagonism Physiological processes mediated by the receptor include:
CNS: neuronal excitation, behavioral effects, learning and anxiety
Smooth muscle: contraction (in gastrointestinal tract & bronchi)
Vasoconstriction/vasodilation
Platelets: aggregation
Activation of the 5-HT2$_A$ receptor with 1-[2,5-dimethoxy-4-iodophyryl]-2-amino propane hydrochloride (DOI), produces potent anti-inflammatory effects in several tissues including cardiovascular and gut. Other 5-HT$_{2A}$ agonists like LSD also have potent anti-inflammatory effects against TNF-alpha-induced inflammation.
Activation of the 5-HT$_{2A}$ receptor in hypothalamus causes increases in hormonal levels of oxytocin, prolactin, ACTH, corticosterone, and renin.
Role in memory Unless specified to the contrary, the term "Quetiapine" embraces both the free base and pharmaceutically acceptable salts thereof.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made. Pharmaceutically acceptable cations include the cationic component of the acids listed above. Pharmaceutically acceptable anions include the anionic component of the bases listed above. In some preferred embodiments, Quetiapine (or a derivative thereof) is formulated as the salt, for instance the fumarate salt. Acids like fumaric acid, because they contain two acidic protons, may form salts with quetiapine in a 1:1 or 2:1 (quetiapine:acid) stoichiometric ratio.

Pharmaceutically acceptable esters include those in which the ester group can be cleaved subsequent to administration and absorption of the quetiapine ester. Esters may be formed through the primary hydroxyl group in quetiapine and a suitable carboxylic acid, and have the following structure:

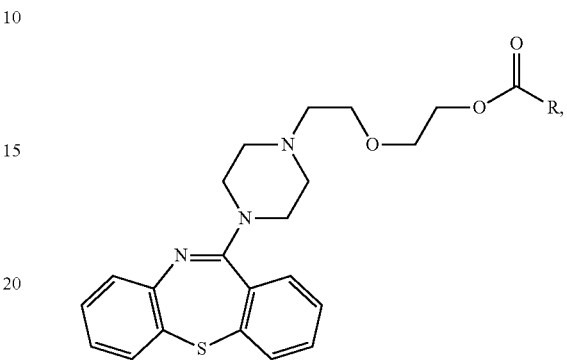

wherein R can be an optionally substituted C$_{1-6}$alkyl group (e.g., methyl, ethyl, propyl, etc). Suitable substituents include hydroxyl, amino, or 1-yl-morpholino groups. In some cases, the ester can be formed using an amino acid, in which cases R is a group of the formula: CH(NH$_2$)R$^1$, wherein R$^1$ can be hydrogen or an optionally substituted C$_{1-6}$alkyl group (e.g, methyl, isopropyl, isobutyl, 3-aminopropyl, benzyl, or 1-mercaptomethyl. Suitable amino acid based esters can be formed from alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of pulmonary arterial hypertension. Within the meaning of the present invention, the term "treat" also includes to arrest, delay the onset (i.e., the period prior to clinical manifestation of a disease) and/or reduce the risk of developing or worsening a disease. The term "combination" as used herein, defines either a fixed combination in one dosage unit form, a non-fixed combination or a kit containing individual parts for combined administration.

Pulmonary hypertension can be classified as either primary or secondary. When the arterial hypertension is not accompanied or caused by another underlying heart or lung disease or condition, it is called primary pulmonary arterial hypertension. When the arterial hypertension is triggered by another disease state, it is designated secondary aterial pulmonary hypertension. Exemplary conditions which can cause secondary pulmonary hypertension include congenital heart defects, ventricular or atrial septal defects/holes, which are in some cases called Eisenmenger complex, as well as valve conditions such as stenosis.

Pulmonary hypertension can be associated with left heart disease, or right heart disease. In some embodiments, Quetiapine (or a derivative thereof) can be used to treat pulmonary hypertension associated with left heart disease, whereas in other embodiments, Quetiapine (or a derivative thereof) can be used to treat pulmonary hypertension associated with right heart disease. In further embodiments, Quetiapine (or a derivative thereof) can be used to treat pulmonary hypertension associated with both right and left heart disease. Quetiapine can be used to treat patients with sporadic idiopathic PAH, heritable PAH, as well as PAH due to disease of small pulmonary muscular arterioles.

Disclosed herein are methods for treating patients with pulmonary arterial hypertension. The hypertension may be mild (resting arterial pressure between 14-25 mm Hg) or complete (resting arterial pressure greater than 25 mm Hg). The patient to be treated may have a pulmonary arterial pressure greater than 14 mm Hg, greater than 16 mm Hg, greater than 18 mm Hg, greater than 20 mm Hg, greater than 22 mm Hg, greater than 24 mm Hg, greater than 26 mm Hg, greater than 28 mm Hg, greater than 30 mm Hg, greater than 32 mm Hg, greater than 34 mm Hg, greater than 36 mm Hg, greater than 38 mm Hg, or greater than 40 mm Hg.

In some embodiments, Quetiapine (or a derivative thereof) is administered to a patient (which may be a human or other mammal) in an amount sufficient to cause at least a 5%, 10%, 15%, 20%, 25%, 30%, 35%, or 40% reduction in resting arterial pressure relative to the pulmonary arterial pressure prior to commencing treatment. In some instances, Quetiapine (or a derivative thereof) is administered at a dose effective such that the patient's final resting arterial pressure is about 25 mm Hg, about 24 mm Hg, about 23 mm Hg, about 22 mm Hg, about 21 mm Hg, about 20 mm Hg, about 19 mm Hg, about 18 mm Hg, about 17 mm Hg, about 16 mm Hg, about 15 mm Hg, or about 14 mm Hg. In certain embodiments, Quetiapine (or a derivative thereof) is administered in combination with other agents, as described below, to achieve these therapeutic outcomes.

Pulmonary hypertension can be characterized by a pulmonary blood pressure greater than about 25 mm Hg at rest, and 30 mm Hg during exercise. Normal pulmonary arterial pressure is about 14 mm Hg at rest. In certain embodiments, Quetiapine (or a derivative thereof) can be used to treat patients having a resting pulmonary arterial pressure of at least 20 mm Hg, at least 25 mm Hg, at least 30 mm Hg, at least 35 mm Hg, at least 40 mm Hg, at least 45 mm Hg, at least 50 mm Hg, at least 55 mm Hg, or at least 60 mm Hg.

In some instances, the Quetiapine may be administered to a patient a single time, while in other cases Quetiapine can be administered using an intervallic dosing regimen. For instance, Quetiapine may be administered once, twice, or three times a day for a period at least 1 week, for example 2 weeks, 4 weeks, 6 weeks, 8 weeks, 10 weeks, 20 weeks, 40 weeks, or 52 weeks. In some instances, Quetiapine administration can be suspended for some period of time (e.g., 1, 2, 3, 4, 6, 8, 10, 20, 40 or 52 weeks) followed by another period of administration.

In some instances, an initial dosage (higher dose, relative to maintenance dose) and maintenance doses (lower dose, relative to initial dose) may be specified. For instance, an initial dosage may be administered over the course of 1, 3, 5, 7, 10, 14, 21 or 28 days, followed by a maintenance dosage which is administered for the duration of the treatment. In some instances, the Quetiapine can be administered to the patient using an interval greater than a day. For instance, the Quetiapine can be administered once every other day, once every third day, once a week, once every two weeks, once every four weeks, once a month, once every other month, once every third month, once every six months, or once a year. In some instance injectable formulations, such as depot formulations, are suitable for dosing regimens with extended periods in between administration, however, oral formulations can also be used in such systems.

The dosage and dosage regimen may be calculated per kg body weight. The dosage regimen may vary from a day to a month. Preferably, the composition as contemplated by the invention may be administered at least once, twice or thrice a day in the dosing range from 0.05 mg to about 20 mg per kg per day, 0.1 mg to about 10 mg per kg per day, 0.5 mg to about 10 mg per kg per day, 0.5 mg to about 5 mg per kg per day, 1 mg to about 5 mg per kg per day, or as per the requirement of the patient to be treated.

In some instances, the Quetiapine (or a derivative thereof) may be administered to a patient a single time, while in other cases Quetiapine (or a derivative thereof) can be administered using an intervallic dosing regimen. For instance, Quetiapine (or a derivative thereof) may be administered once, twice, or three times a day for a period at least 1 week, for example 2 weeks, 4 weeks, 6 weeks, 8 weeks, 10 weeks, 20 weeks, 40 weeks, or 52 weeks. In some instances, Quetiapine (or a derivative thereof) administration can be suspended for some period of time (e.g., 1, 2, 3, 4, 6, 8, 10, 20, 40 or 52 weeks) followed by another period of administration.

Preferably, Quetiapine (or a derivative thereof) may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention.

In some instances, Quetiapine (or a derivative thereof) can be administered by inhalation, for instance as a powder or aerosolizable formulation.

The bioavailability of the drug in a composition, depends on various attributes of the drug as well as the other inactive ingredients in the formulation. The particle size of the drug is one of such attribute that may affect the bioavailability of the drug, when administered to a patient. The particle size may thus be adjusted as per the requirements of the invention.

The inventors of the present invention have also found that the solubility properties of Quetiapine (or a derivative thereof) may be improved by nanosizing thus leading to better bioavailability and dose reduction of the drug.

In one embodiment, Quetiapine (or a derivative thereof) may be present in the form of nanoparticles which have an average particle size of less than 2000 nm, less than 1500 nm, less than 1000 nm, less than 750 nm, or less than 500 nm.

Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

In some instances, the Quetiapine (or a derivative thereof) can be administered to the patient using an interval greater than a day. For instance, the Quetiapine (or a derivative thereof) can be administered once every other day, once every third day, once a week, once every two weeks, once every four weeks, once a month, once every other month, once every third month, once every six months, or once a year. In some instance injectable formulations, such as depot formulations, are suitable for dosing regimens with extended periods in between administration, however, oral formulations can also be used in such systems.

In some embodiments, pulmonary arterial hypertension can be alleviated or treated by administration of Quetiapine (or a derivative thereof) in combination with one or more other drugs either simultaneously, sequentially, or separately.

Preferably, one or more standard of care drugs that may be envisaged under the scope of the present invention may comprise from categories of for the treatment of pulmonary hypertension such as, but not limited to phosphodiesterase inhibitors, endothelin receptor antagonist, Inotropic agents, and stimulators of soluble guanylate cyclase, such as riociguat.

Specifically, one or more standard of care drugs include but not limited to sildenafil, tadalafil, bosentan, ambrisentan, macitentan, nifedipine, diltiazem, digoxin. There are others which dilate the pulmonary arteries and prevent blood clot formation. Examples of such drugs are Epoprostenol (Veletri, Flolan), treprostinil sodium (Remodulin, Tyvaso), iloprost (Ventavis); PDE 5 inhibitors such as Sildenafil (Revatio), tadalafil (Adcirca), relaxes pulmonary smooth muscle cells, which leads to dilation of the pulmonary arteries.

The use of Quetiapine may preferably be associated with one or more of the above referenced drugs as a combination therapy (either of the same functional class or other) depending on various factors like drug-drug compatibility, patient compliance and other such factors wherein the said combination therapy may be administered either simultaneously, sequentially, or separately for the treatment of PAH.

Quetiapine (or a derivative thereof) may be provided with one or more drugs in the form of a kit, wherein the kit includes Quetiapine and at least one other drug, and instructions for their administration to a PAH patient.

In certain embodiments, the administration of Quetiapine (or a derivative thereof), either alone or in combination with one or more drugs selected from but not limited to phosphodiesterase inhibitors such as sildenafil, tadalafil etc., endothelin receptor antagonist such as bosentan, macitentan etc. and stimulators of soluble guanylate cyclase such as riociguat. In certain embodiments, Quetiapine (or a derivative thereof) can be co-administered with one or more additional agents effective to lower pulmonary hypertension. In some embodiments the co-administration includes a unitary dosage form containing Quetiapine (or a derivative thereof) and at least one more agent. In other embodiments, Quetiapine (or a derivative thereof) is administered separately from the other agent(s). The additional agent can be a PDE-5 inhibitor, for example, avanafil, lodenafil, mirodenafil, sildenafil, tadalafil, vardenafil, udenafil, zaprinast, or icariin. Other agents include calcium channel blockers like dihydropyridines (e.g., amlodipine, nifefipine) and diltiazem; prostacyclin pathway agonists such as epoprostenol, treprostinil, iloprost, and selexipag; endothelin receptor antagonists such as bosentan, macitentan, ambrisentan, andsitaxsentan; guanylate cyclase stimulators such as riociguat; diuretics; toprimate; fusadil; or anti-coagulants like warfarin.

It may be well appreciated by a person skilled in the art that the pharmaceutical composition comprising Quetiapine in combination with one or more drugs may require specific dosage amounts and specific frequency of administrations specifically considering their individual established doses, the dosing frequency, patient adherence and the regimen adopted. As described herein, considering that there are various parameters to govern the dosage and administration of the combination composition as per the present invention, it would be well acknowledged by a person skilled in the art to exercise caution with respect to the dosage, specifically, for special populations associated with other disorders.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1—Pulmonary Arterial Hypertension Efficacy Model: Monocrotaline Rat

The studies were conducted for hemodynamic evaluation of quetiapine in anesthetized sprague dawley rats treated with monocrotaline ("MCT") to induce pulmonary arterial hypertension. Sildenafil was used as an internal control to compare the effects of Quetiapine.

The effects of Quetiapine were evaluated in rats with monocrotaline induced pulmonary arterial hypertension using sildenafil as standard care treatment. Male Sprague-Dawley rats were orally administered vehicle, Quetiapine (40 mg/kg, divided into a BID regimen given every day for 28 days starting on Day 1), or sildenafil (100 mg/kg, administered once daily) (n=12 in each group). Rats received a single injection of monocrotaline (50 mg/kg, s.c.) on Study Day 1. On the twenty-eighth day following monocrotaline dosing, the rats were anesthetized with ketamine/xylazine for terminal monitoring of pulmonary and systemic arterial pressures along with heart rate.

Test Item:
Vehicle (0.5% Methylcellulose+0.2% Tween 80 in deionized water, Quetiapine (40 mg/kg dib for 28 days; Sildenafil (1000 mg/kg, administered once daily)
Route of Administration:
Oral
* is 0.5% methyl cellulose+0.2% Tween 80 in deionized water
Study Design:
The study was planned and conducted according to design depicted below in Table 1

TABLE 1

Study Design

| Group No | Group Name | N | MCT (S.C) | Test Compound | Dose (P.O) | Dosing |
|---|---|---|---|---|---|---|
| Group I | Negative control | 12 | — | Vehicle | 1 mL/kg | QD |
| Group II | Control | 12 | 50 mg/kg | MCT | — | — |
| Group III | Positive Control | 12 | 50 mg/kg | Vehicle | 1 mL/kg | QD |
| Group IV | Test | 12 | 50 mg/kg | Quetiapine | 40 mg/kg | BID |
| Group V | Standard | 12 | 50 mg/kg | Sildenafil | 100 mg/kg | QD |

Male Sprague-Dawley rats in groups I, II, III and IV and V were administered 50 mg/kg of body weight of Monocrotaline in DMSO subcutaneously to induce PAH on day 1. The DMSO group (Group I, negative control) received a single dose of DMSO subcutaneously on day 1. The vehicle group received 5 ml of vehicle every morning. The Quetiapine as well as sildenafil groups were orally administered Quetiapine (40 mg/kg, divided into a BID regimen given every day for 28 days starting on Day 1), or sildenafil (100 mg/kg, administered once daily). On the twenty-eighth day after monocrotaline dosing, the rats were anesthetized with ketamine/xylazine for terminal monitoring of pulmonary and systemic arterial pressures along with heart rate.

Observation:
There were differences in systolic and mean pulmonary arterial pressures after 28 days in rats treated with Quetiapine at 40 mg/kg/day given bid as compared to the vehicle group.

Results:
Body weights among the vehicle and treatment cohorts were not significantly different at Study Day 28. There were differences in systolic and mean pulmonary arterial pressures after 28 days in rats treated with 40 mg/kg/bid Quetiapine compared to the vehicle group.

The results are depicted in Table 2 (Right Ventricular Systolic Pressure); Table 3 (Right Ventricular Pressure) and Table 4 (Fulton index: Hypertrophy (RV/LV+S))

TABLE 2

Right Ventricular Systolic Pressure
Right Ventricular Systolic Pressure (RVSP) mmHg

| Negative Control | Control | Positive Control | Quetiapine (40 mg/Kg bid) | Sildenafil (100 mg/kg) |
|---|---|---|---|---|
| 20.652 | 58.059 | 70.816 | 37.045 | 34.262 |
| 25.143 | 81.052 | 61.444 | 44.925 | 25.579 |
| 17.995 | 57.290 | 77.630 | 54.140 | 33.864 |
| 27.854 | 78.538 | 59.801 | 47.463 | 23.627 |
| 25.161 | 62.606 | 72.949 | 43.052 | 31.322 |
| 21.357 | 60.018 | 60.142 | 36.213 | 24.486 |
| 20.936 | 72.695 | 56.082 | 41.515 | 29.450 |
| 23.622 | 57.327 | 68.670 | 68.747 | 31.316 |
| 24.461 | | | 54.503 | 32.922 |
| 25.580 | | | | |
| 26.098 | | | | |
| 20.773 | | | | |

|  | Negative Control | Control | Positive Control | Quetiapine (40 mg/Kg bid) | Sildenafil (100 mg/kg) |
|---|---|---|---|---|---|
| Mean | 23.303 | 65.948 | 65.942 | 47.511 | 29.648 |
| SD | 2.907 | 9.928 | 7.613 | 10.268 | 4.106 |
| SE | 0.839 | 3.510 | 2.692 | 3.423 | 1.369 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 3

Right Ventricular Pressure
Right Ventricular Systolic Pressure (RVSP) mmHg

| Negative Control | Control | Positive Control | Quetiapine (40 mg/Kg bid) | Sildenafil (100 mg/kg) |
|---|---|---|---|---|
| 9.656 | 30.124 | 32.476 | 18.440 | 12.947 |
| 12.987 | 36.451 | 30.376 | 20.951 | 12.352 |
| 9.102 | 27.676 | 37.232 | 27.940 | 16.804 |
| 16.666 | 33.807 | 31.187 | 21.646 | 11.481 |
| 12.701 | 29.169 | 30.585 | 22.967 | 15.226 |
| 9.210 | 30.734 | 31.389 | 16.792 | 11.673 |
| 8.251 | 29.384 | 28.909 | 19.956 | 14.427 |
| 11.448 | 28.386 | 31.214 | 24.109 | 14.139 |
| 12.402 | | | 28.929 | 16.310 |
| 12.866 | | | | |
| 10.947 | | | | |
| 9.645 | | | | |

|  | Negative Control | Control | Positive Control | Quetiapine (40 mg/Kg bid) | Sildenafil (100 mg/kg) |
|---|---|---|---|---|---|
| Mean | 11.323 | 30.716 | 31.671 | 22.414 | 13.929 |
| SD | 2.361 | 2.967 | 2.466 | 4.067 | 1.951 |
| SE | 0.682 | 1.049 | 0.872 | 1.356 | 0.650 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 4

Fulton index: Hypertrophy (RV/LV + S)
Right Ventricular Systolic Pressure (RVSP) mmHg

| Negative Control | Control | Positive Control | Quetiapine (40 mg/Kg bid) | Sildenafil (100 mg/kg) |
|---|---|---|---|---|
| 0.181 | 0.619 | 0.604 | 0.378 | 0.330 |
| 0.179 | 0.482 | 0.499 | 0.334 | 0.167 |
| 0.166 | 0.493 | 0.518 | 0.534 | 0.354 |
| 0.180 | 0.471 | 0.534 | 0.458 | 0.367 |
| 0.206 | 0.588 | 0.614 | 0.438 | 0.297 |
| 0.200 | 0.426 | 0.508 | 0.356 | 0.323 |
| 0.202 | 0.513 | 0.483 | 0.336 | 0.312 |
| 0.211 | 0.494 | 0.446 | 0.601 | 0.352 |
| 0.162 | | | 0.289 | 0.309 |
| 0.228 | | | | |
| 0.213 | | | | |
| 0.231 | | | | |

TABLE 4-continued

Fulton index: Hypertrophy (RV/LV + S)
Right Ventricular Systolic Pressure (RVSP) mmHg

|  | Negative Control | Control | Positive Control | Quetiapine (40 mg/Kg bid) | Sildenafil (100 mg/kg) |
|---|---|---|---|---|---|
| Mean | 0.197 | 0.511 | 0.526 | 0.414 | 0.312 |
| SD | 0.023 | 0.063 | 0.058 | 0.103 | 0.059 |
| SE | 0.007 | 0.022 | 0.020 | 0.034 | 0.020 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control.

TABLE 5

Right Ventricle
Right Ventricle (RV) (g)

|  | Negative Control | Control | Positive Control | Quetiapine (40 mg/Kg bid) | Sildenafil (100 mg/kg) |
|---|---|---|---|---|---|
|  | 0.160 | 0.337 | 0.378 | 0.276 | 0.261 |
|  | 0.178 | 0.336 | 0.320 | 0.190 | 0.083 |
|  | 0.127 | 0.227 | 0.300 | 0.336 | 0.236 |
|  | 0.140 | 0.327 | 0.390 | 0.337 | 0.440 |
|  | 0.180 | 0.347 | 0.419 | 0.312 | 0.228 |
|  | 0.180 | 0.349 | 0.322 | 0.260 | 0.207 |
|  | 0.190 | 0.317 | 0.387 | 0.193 | 0.232 |
|  | 0.177 | 0.386 | 0.333 | 0.353 | 0.308 |
|  | 0.124 |  |  | 0.225 | 0.229 |
|  | 0.185 |  |  |  |  |
|  | 0.170 |  |  |  |  |
|  | 0.205 |  |  |  |  |
| Mean | 0.168 | 0.328 | 0.356 | 0.276 | 0.247 |
| SD | 0.025 | 0.046 | 0.043 | 0.063 | 0.094 |
| SE | 0.007 | 0.016 | 0.015 | 0.021 | 0.031 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control.

TABLE 6

Right Ventricle/Body Weight
Right Ventricle (RV) (g)

|  | Negative Control | Control | Positive Control | Quetiapine (40 mg/Kg bid) | Sildenafil (100 mg/kg) |
|---|---|---|---|---|---|
|  | 0.0004 | 0.0010 | 0.0012 | 0.0008 | 0.0007 |
|  | 0.0004 | 0.0010 | 0.0009 | 0.0006 | 0.0003 |
|  | 0.0003 | 0.0009 | 0.0009 | 0.0010 | 0.0007 |
|  | 0.0004 | 0.0009 | 0.0012 | 0.0010 | 0.0009 |
|  | 0.0004 | 0.0010 | 0.0012 | 0.0010 | 0.0006 |
|  | 0.0004 | 0.0009 | 0.0008 | 0.0007 | 0.0006 |
|  | 0.0004 | 0.0008 | 0.0009 | 0.0006 | 0.0006 |
|  | 0.0005 | 0.0009 | 0.0008 | 0.0012 | 0.0007 |
|  | 0.0003 |  |  | 0.0006 | 0.0006 |
|  | 0.0004 |  |  |  |  |
|  | 0.0004 |  |  |  |  |
|  | 0.0004 |  |  |  |  |
| Mean | 0.0004 | 0.0009 | 0.0010 | 0.0008 | 0.0006 |
| SD | 0.0000 | 0.0001 | 0.0002 | 0.0002 | 0.0002 |
| SE | 0.0000 | 0.0000 | 0.0001 | 0.0001 | 0.0001 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control The results suggest that Quetiapine activity in controlling or reducing PAH was found to be comparable among with Sildenafil activity.

Example 2: Quetiapine Fumarate Tablet Composition

| Sr. No. | Ingredients | Qty/Tab (mg) |
|---|---|---|
| 1 | Quetiapine Fumarate | 10-500 |
| 2 | Microcrystalline cellulose | 10-200 |
| 3 | Dicalcium Phosphate | 50-200 |
| 4 | Croscarmellose Sodium | 2-20 |
| 5 | Povidone | 3-25 |
| 6 | Polysorbate 80 | 3-10 |
| 7 | Methylene chloride/water | q.s. |
| 8 | Hypromellose | 30-90 |
| 9 | Colloidal silicon dioxide | 1-5 |
| 10 | Talc | 1-5 |
| 11 | Magnesium Stearate | 1-5 |
|  | Coating |  |
| 12 | Opadry ready mix | 10-20 |
| 13 | Purified water | q.s. |

Manufacturing Process
1. Microcrystalline cellulose, Dibasic calcium Phosphate and Croscarmellose sodium were sifted through #35 sieve (500 microns) and collected in a polyelylene bag.
2. Quetiapine fumarate was sifted through #60 sieve (250 micron) and collected in a polyelylene bag.
3. The materials of step 1 & 2 were loaded in a suitable mixer granulator (Rapid Mixer Granulator) and mixed for 10 minutes.
4. Polysorbate-80 solution was prepared by dissolving in polysorbate-80 in half quantity of methylene chloride/water under stirring.
5. Binder solution was prepared by dissolving povidone in remaining quantity of methylene chloride/water under stirring. Mix the solution of step to a solution of step 5 under stirring.
6. The dry mix of step 3 was then granulated with the binder solution of step 5 in a rapid mixer granulator till the wet mass of suitable consistency was obtained.
7. The granules were then dried in a fluidized bed drier a until the desired LOD was achieved.
8. Sizing of the dried granules was done by passing through #22 sieve.
9. Blending of the granules of step 8 with Hypromellose (previously sifted through 40 # sieve), silicon dioxide (sifted through #80 sieve) and talc (sifted through #80 sieve) for 10-15 minutes in an octagonal blender.
10. The required quantity of Magnesium stearate was weighed and sifted through #80 sieve and added to the blend of step 9 and blended for 3-7 minutes.
11. The blend of step 10 was then compressed in to tablets using suitable punches using tablet compression machine.
12. The compressed tablets were then film coated with Opadry ready mix using a tablet coating machine.

Example 3: Quetiapine Fumarate Extended Release Tablets

| Sr. No | Ingredients | Qty (mg/tab) |
|---|---|---|
| 1. | Quetiapine Fumarate | 10-500 |
| 2. | Microcrystalline cellulose | 75-200 |
| 3. | Lactose | 75-200 |
| 4. | Povidone | 4-16 |
| 5. | Corn Starch | 10-45 |

-continued

| Sr. No | Ingredients | Qty (mg/tab) |
|---|---|---|
| 6. | Purified water | Q.s. |
| 7. | Hypromellose (HPMC K4M/K15 M/K100 M) | 150-750 |
| 8. | Colloidal silicon dioxide | 1-6 |
| 9. | Talc | 3-12 |
| 10. | Magnesium Stearate | 3-12 |
| 11 | Ready mix opadry | 5-10 |
| 12 | Purified water | Q.s. |

Manufacturing Process

1. Binder solution was prepared by dissolving Povidone in purified water.
2. Quetiapine fumarate, Microcrystalline cellulose, Lactose and Hypromellose were sifted through #30 mesh sieve.
3. The sifted materials of step 2 were then placed in rapid mixer granulator and dry mixing carried out for 10 mins.
4. The dry mix was further granulated using the binder of step 1.
5. Granules were then dried in a fluid bed drier until the desired LOD was achieved.
6. Sizing of the granules was done by passing the dried granulator through multimill.
7. The dried sized granules were then blended with Colloidal silicon dioxide and talc (pre-sifted through #80 sieve) followed by lubrication with magnesium stearate (pre-sifted through #80 sieve) in an Octagonal blender.
8. The lubricated blend was then compressed into tablets using suitable tooling using a tablet compression machine.
9. The tablets were further film coated using a film coating dispersion. (The film coating dispersion was prepared by dispersing the Opadry dry mix in purified water).

Example 4: Quetiapine Fumarate Tablets

| Sr. No. | Ingredients | Quantity mg/tablet |
|---|---|---|
| 1. | Quetiapine Fumarate | 10-500 |
| 2. | Carnauba wax | 30-300 |
| 3. | Glyceryl dibehenate | 10-60 |
| 4. | Colloidal silicon dioxide | 0.25-2.5 |
| 5. | Magnesium stearate | 3-10 |
| 6. | Surelese coating (Colorcon) | 5-25 |
| 7. | Purified water | QST |

Manufacturing Process

1. Quetiapine is mixed with carnauba wax and hot melt granulated.
2. The granulate of step 1 is then milled.
3. The milled granules are then blended with colloidal silicon di-oxide and magnesium stearate.
4. The blend was then compressed into tablets using a tablet compression machine
5. The compressed tablets were further coated using Surelese coating dispersion in purified water in a suitable coating machine.

Example 5: Quetiapine Fumarate Delayed Release Tablets

| Sr. No. | Ingredients | Quantity mg/tablet |
|---|---|---|
| | Granulation | |
| 1. | Quetiapine Fumarate | 10-500 |
| 2. | Povidone | 10-60 |
| 3. | Stearic acid | 2.5-100 |
| | Coating | 0.25-2.5 |
| 4. | Ethocel PR 100 (Ethylcellulose) | 5-25 |
| 5. | Povidone | 5-15 |
| 6. | Polyethylene glycol 1450 | 2.5-10 |
| 7. | Denatured alcohol | Q.s. |

Manufacturing Process

1. Povidone was dissolved in water.
2. Quetiapine was placed in top-spray assembly of the Fluid bed processor (GPCG 1-1).
3. Povidone solution was then sprayed on to the active to form granules.
4. Sizing of the granules was done by passing through the suitable sieve.
5. Stearic acid was weighed and sifted through a suitable sieve.
6. The milled granules were then blended with stearic acid in a suitable blender.
7. The blend was then compressed into tablets using a tablet compression machine
8. The compressed tablets were further coated using Surelese coating dispersion in purified water in a suitable coating machine Example 6: Powder for Oral Suspension

| Sr. No. | Ingredients | Quantity mg/ml |
|---|---|---|
| 1. | Quetiapine Fumarate | 10-500 |
| 2. | Xylitol | 100-400 |
| 3. | Citric acid monohydrate | 1-10 |
| 4. | Sucralose | 0.1-7.5 |
| 5. | Xanthan gum | 0.1-1.0 |
| 6. | Talc | 0.25-2.5 |
| 7. | Magnesium stearate | 0.5-2.5 |
| 8. | Colloidal silicon dioxide | 5-10 |
| 9. | Artificial Cherry Flavour | 5-10 |

Manufacturing Process

1. Quetiapine fumarate was sifted through sieve #60 and collected in a polyethylene bag
2. Xylitol and citric acid monohydrate was weighed and sifted through sieve #40 and collected in a suitable polybag
3. Sucralose, xanthan gum, Artificial cherry flavor were sifted through sieve #60 and collected in a suitable polyethylene bag
4. Talc, Magnesium stearate, and colloidal silicon-di-oxide were sifted through sieve #80 and collected in a polyethylene bag
5. The quetiapine fumarate, Xylitol, Citric acid monohydrate, Sucralose, Xanthan gum, Talc and colloidal silicon dioxide were placed in a suitable blender and blended for 10 minutes.

6. Artificial cherry flavor and magnesium stearate was added to the blend of step 5 and further blended for 5 minutes.
7. The blend was then filled in high density HDPE bottles and sealed with CRC caps using induction sealer.

Example 7: Quetiapine Soft Gelatin Capsule Composition

| Sr. No. | Ingredient | Qty. mg/unit |
|---|---|---|
| 1. | Quetiapine Fumarate | 20-400 |
| 2. | D-alpha-tocopheryl polyethylene glycol 1000 succinate (TPGS) | 250-550 |
| 3. | Polyethylene glycol 400 | 250-400 |
| 4. | Polyethylene glycol 400 | 25-40 |

Manufacturing Process
1. D-alpha-tocopheryl polyethylene glycol 1000 succinate (TPGS) was loaded in a suitable stainless steel jacketed vessel and heated to 50.0 until liquefied.
2. Polyethylene glycol 400 (90%) was heated in a separate stainless steel vessel to 50.0 and added to the liquefied material of step 1 slowly.
3. The ingredients were mixed using a suitable stirrer until homogenous solution obtained.
4. The temperature of the homogenous solution was increased to 65° C., and Quetiapine
Fumarate was added to the solution under constant stirring and dissolved.
5. Remaining quantity of Polyethylene glycol 400 (10%) was added to the solution of step 4 and the solution cooled to room temperature.
6. Vacuum was applied to remove the entrapped air.
7. The mixture was then filled using white opaque soft gelatin capsules (size 12, oblong) using a capsule-filling machine. The capsules were further dried to a moisture level of 3-6% and shell hardness of 7-10 N and packed in a suitable container.

Example 8: Oral Suspension

| Sr. No. | Ingredients | Quantity mg/mL |
|---|---|---|
| 1. | Quetiapine Fumarate | 10-500 |
| 2. | Ascorbic acid | 5-15 |
| 3. | Edetate disodium (sodium EDTA) | 0.2-2.0 |
| 4. | Saccharin sodium | 0.1-1.0 |
| 5. | Sodium metabisulfite (sodium disulfite) | 1-5 |
| 6. | Propylene glycol | 75-150 |
| 7. | Sorbitol (70% solution) | 75-150 |
| 8. | Glycerin (glycerol) | 200-350 |
| 9. | Sucrose | 250-400 |
| 10. | Quinoline yellow | 0.01-0.1 |
| 11. | Pineapple flavor | 0.1-0.5 |
| 12. | Purified water | q.s |

Manufacturing Process
1. Purified water (~25% of total quantity required) was added to a manufacturing vessel and heated to 90° C. to 95° C.
2. Required quantity of sucrose was added to the heated water of step 1 under slow mixing (temperature maintained at 90° C. to 95° C.). Mixing was continued for 1 hr.
3. Propylene glycol, sorbitol (70% solution) glycerin was added to the mixture of step 2 and mixed at high speed for 10 minutes.
4. The mixture was allowed to cool to a temperature of 50° C. with continuous mixing at slow speed.
5. Quetiapine fumarate was added to the solution of step 4 with continuous mixing at high speed for 30 minutes until a uniform suspension was obtained.
6. Ascorbic acid, edetate disodium and sodium metabisulfite were added to the suspension of step 4 with continuous mixing.
7. Pineapple flavor was dissolved in part quantity of purified water and added to suspension of step 4 with continuous mixing.
8. Saccharin sodium were dissolved in part quantity of purified water and added to the suspension of step 4 with continuous mixing.
9. Quinoline yellow was dissolved in part quantity of purified water and the colour solution was transferred to the suspension of step 4 with continuous mixing.
10. Rinsing of the container of colour solution was done with purified water and rinsings added to the Suspension of step 4. The mixture was mixed at high speed for 5 minutes.
11. Volume makeup was done with purified water and solution was again mixed for 20 minutes at high speed.
12. pH of the suspension was checked and recorded (limit: 6.0-8.2). If required, pH was adjusted with 10% citric acid or 10% sodium citrate solution.
13. The suspension was then filled in suitable bottles.

Example 9: Capsule Composition

| Sr. No | Ingredients | Qty (mg/tab) |
|---|---|---|
| | Core pellets | |
| 1 | Quetiapine Fumarate | 10-500 |
| 2 | Microcrystalline cellulose | 75-200 |
| 3 | Lactose | 75-200 |
| 5 | Povidone | 2.5-10 |
| 6 | Purified water | Q.s. |
| | Seal coating | |
| 7 | Hypromellose | 15-40 |
| 8 | Triethyl citrate | 0.25-2.5 |
| 9 | Isopropyl alcohol | QS |
| | Functional coating | |
| 10 | Ethyl cellulose | 20-60 |
| 11 | Triethyl citrate | 0.25-2.5 |
| 12 | Talc | 3-12 |
| 13 | Isopropyl alcohol | Q.s. |
| 14 | Purified water | Q.s. |

Manufacturing Process
1. Quetiapine fumarate, Microcrystalline cellulose, Lactose were sifted through #40 mesh sieve.
2. The sifted materials of step 2 were then placed in planetary mixer and dry mixing was done for 10 minutes.
3. Binder solution was prepared by dissolving Povidone in purified water and wetting of the mass was done by adding the binder solution to the dry mixture blend of step 3.
4. The wet mass of step 3 was then passed through extruder to form cylindrical shaped extrudates.
5. The extrudates were then places in a spheronizer to form pellets.
6. Pellets were then dried in a fluid bed drier until the desired LOD was achieved.
7. Seal coating solution was prepared by dissolving HPMC, PVP and Triethyl citrate in a mixture of Isopropyl alcohol and purified water 8. Pellets were then seal-coated with a seal coating solution using fluid bed processor fitted with a bottom spray assembly.
9. The seal coated pellets were further coated with ethyl cellulose dispersion
10. Functional coating dispersion was prepared by dissolving ethyl cellulose and triethyl citrate in isopropyl alcohol, talc was dispersed in purified water and this dispersion was then added to the ethlycellulose solution to form a coating dispersion.
11. Seal coated pellets were then coated with ethyl cellulose dispersion using a fluid bed processor fitted with a bottom spray assembly.
12. The coated pellets were then filled in capsules.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

The invention claimed is:

1. A method of treating pulmonary hypertension in a patient in need thereof, comprising administering to the patient a composition comprising an effective amount of a quetiapine or a pharmaceutically acceptable salt or ester thereof,
   wherein the pulmonary hypertension is pulmonary arterial hypertension.
2. The method of claim 1, wherein the patient has a resting pulmonary arterial pressure greater than 14 mm Hg.
3. The method of claim 1, wherein the patient has a resting pulmonary arterial pressure
   greater than 40 mm Hg.
4. The method of claim 1, wherein quetiapine is administered in an amount effective to lower resting pulmonary arterial blood pressure to a level no greater than 18 mm Hg.
5. The method of claim 1, wherein quetiapine is administered in an amount effective to lower resting pulmonary arterial blood pressure at least 5% relative to the resting
   pulmonary arterial blood pressure prior to commencing treatment.
6. The method of claim 1, wherein quetiapine is administered in a dose from 0.1 to 50 mg.
7. The method of claim 1, wherein the composition comprises quetiapine fumarate.
8. The method of claim 7, wherein the composition is administered orally, by injection, parenterally, buccally, transdermally, or by inhalation.
9. The method of claim 7, wherein the composition is administered orally.
10. The method of claim 7, wherein the composition is administered parenterally.
11. The method of claim 1, further comprising administering at least one additional agent effective to treat pulmonary hypertension.
12. The method of claim 11, wherein the at least one additional agent comprises one or more of phosphodiesterase inhibitors, calcium channel blockers, endothelin receptor antagonists, inotropic agents, prostacyclin pathway agonists, anti-coagulants, guanylate cyclase stimulators, or a combination thereof.
13. The method of claim 11, wherein the at least one additional agent comprises one or more of avanafil, lodenafil, mirodenafil, sildenafil, tadalafil, vardenafil, udenafil, zaprinast, icariin, amlodipine, nifefipine, diltiazem, bosentan, ambrisentan, sitaxsentan, macitentan, riociguat, toprimate, fusadil, warfarin, digoxin, epoprostenol, treprostinil sodium, iloprost, selexipag, or a combination thereof.

* * * * *